(12) United States Patent
Shingu et al.

(10) Patent No.: US 6,626,881 B2
(45) Date of Patent: Sep. 30, 2003

(54) DISPOSABLE DIAPER

(75) Inventors: Yoshikazu Shingu, Kagawa-ken (JP); Hirotomo Mukai, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/871,018

(22) Filed: May 31, 2001

(65) Prior Publication Data

US 2001/0056271 A1 Dec. 27, 2001

(30) Foreign Application Priority Data

Jun. 19, 2000 (JP) ........................................ 2000-183701

(51) Int. Cl.⁷ ................................................ A61F 13/15
(52) U.S. Cl. ...................... 604/385.201; 624/385.28; 624/385.04
(58) Field of Search .................. 604/385.28, 385.01, 604/389, 391, 392, 387, 385.201, 385.03

(56) References Cited

U.S. PATENT DOCUMENTS

| | | | | |
|---|---|---|---|---|
| 3,863,637 A | * | 2/1975 | MacDonald et al. | ........ 604/365 |
| 3,890,973 A | * | 6/1975 | Davis et al. | ................. 604/355 |
| 3,943,930 A | * | 3/1976 | Schaar | ........................ 604/365 |
| 4,108,179 A | * | 8/1978 | Schaar | ................ 604/385.201 |
| 4,237,890 A | * | 12/1980 | Laplanche | ................... 128/287 |
| 4,808,178 A | * | 2/1989 | Aziz et al. | ............. 604/385.28 |
| 5,053,028 A | * | 10/1991 | Zoia et al. | ................ 604/385.1 |
| 5,318,555 A | * | 6/1994 | Siebers et al. | .............. 604/390 |
| 5,496,428 A | * | 3/1996 | Sageser et al. | ............ 156/73.1 |
| 5,542,943 A | * | 8/1996 | Sageser | ................. 604/385.28 |
| 5,624,428 A | * | 4/1997 | Sauer | .......................... 604/391 |
| 5,752,947 A | * | 5/1998 | Awolin | ....................... 604/387 |
| 6,213,991 B1 | * | 4/2001 | Kling et al. | ........... 604/385.01 |

* cited by examiner

*Primary Examiner*—Weilun Lo
*Assistant Examiner*—Jacqueline F Stephens
(74) *Attorney, Agent, or Firm*—Butzel Long

(57) ABSTRACT

A disposable diaper includes a pair of rear wings formed in a rear waist region of the diaper, the rear wings are folded twice or more on the inner side of the diaper so that free side edge portions of the rear wings may extend outward circumferentially of the diaper's body.

6 Claims, 5 Drawing Sheets

DISPOSABLE DIAPER

BACKGROUND OF THE INVENTION

This invention relates to a disposable diaper and more particularly to such a diaper adapted to be easily put on a wearer's body even if the wearer is a bedridden adult.

Conventional disposable diapers are formed in a front or rear waist region with a pair of wings extending outward in a circumferential direction. Such known diaper is compactly folded in a longitudinal direction in two or three after the wings have been folded back onto the inner side of the wings and supplied to consumer in such compact state.

When it is desired to unfold this compactly folded diaper to put it on a wearer's body, it will be difficult to place the wearer's hip upon a transversely middle portion of the diaper if the wearer is an adult, particularly a bedridden adult having a relatively heavy body weight.

SUMMARY OF THE INVENTION

It is an object of this invention to provide a disposable diaper adapted to be easily put on a wearer's body by placing the wearer's hip on a transversely middle portion of the diaper even if the wearer is a bedridden adult.

According to this invention, there is provided a disposable diaper comprising a liquid-pervious topsheet, a liquid-impervious backsheet and a liquid-absorbent core disposed between these two sheets so as to configure a front waist region, a rear waist region and a crotch region extending between these two waist regions in a longitudinal direction of the diaper wherein the rear waist region is formed on transversely opposite sides thereof with first wings extending outward in a circumferential direction intersecting the longitudinal direction.

The improvement according to this invention is in that the first wings have proximal side edge portions extending in the longitudinal direction immediately outside transversely opposite side edges of the core and free side edge portions spaced apart from the side edges of the core and opposed to the respective proximal side edge portions wherein the first wings are folded on an inner side of the diaper along fold lines extending in the longitudinal direction twice or more so that the free side edge portions extend outward in the circumferential direction.

DETAILED DESCRIPTION OF THE PREFERRED EMBODIMENTS

Details of a disposable diaper according to this invention will be more fully understood from the description given hereunder with reference to the accompanying drawings.

Figure 1:
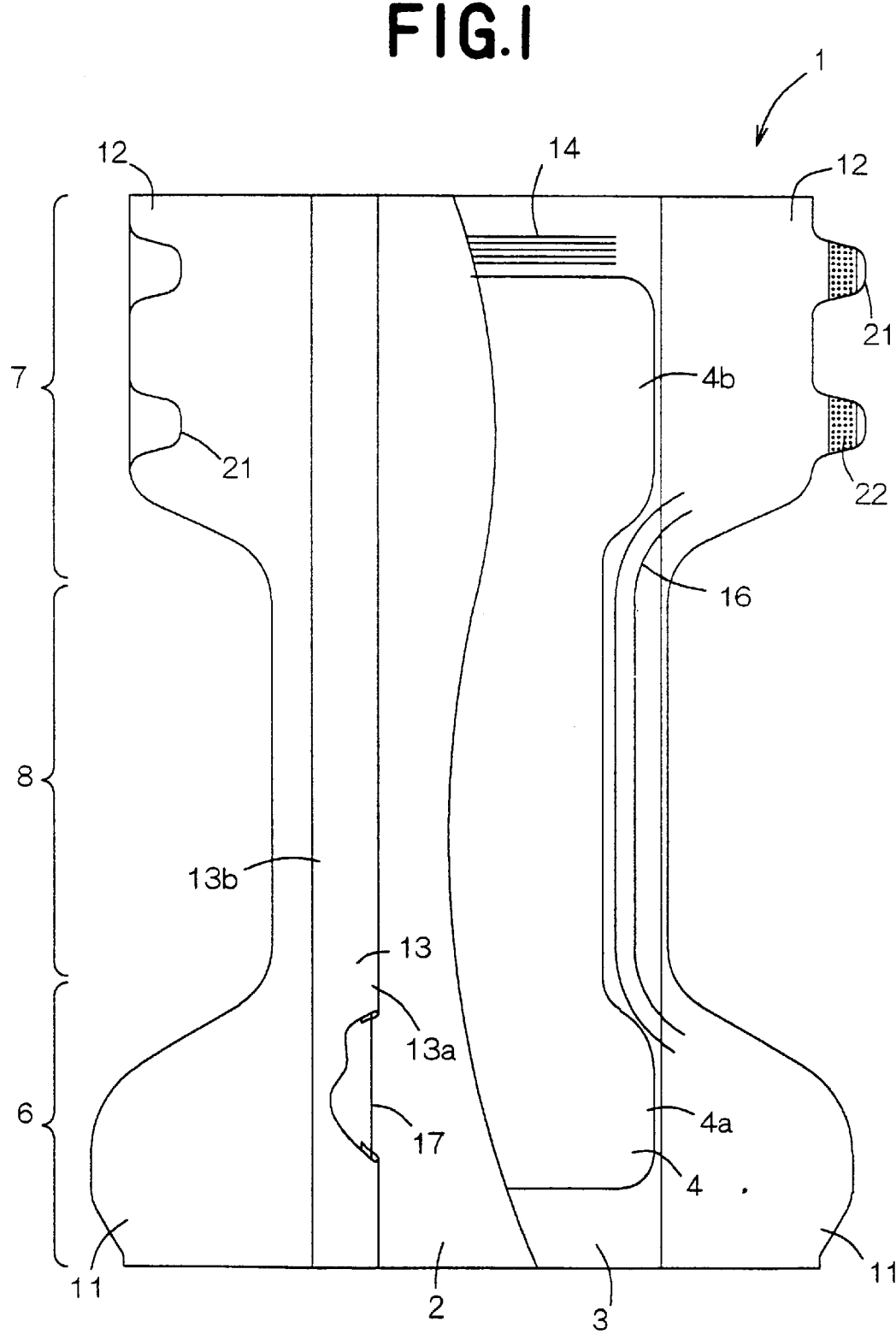
FIG. 1 is a plan view showing an inner side of a disposable diaper as partially broken away.
Figure 2:
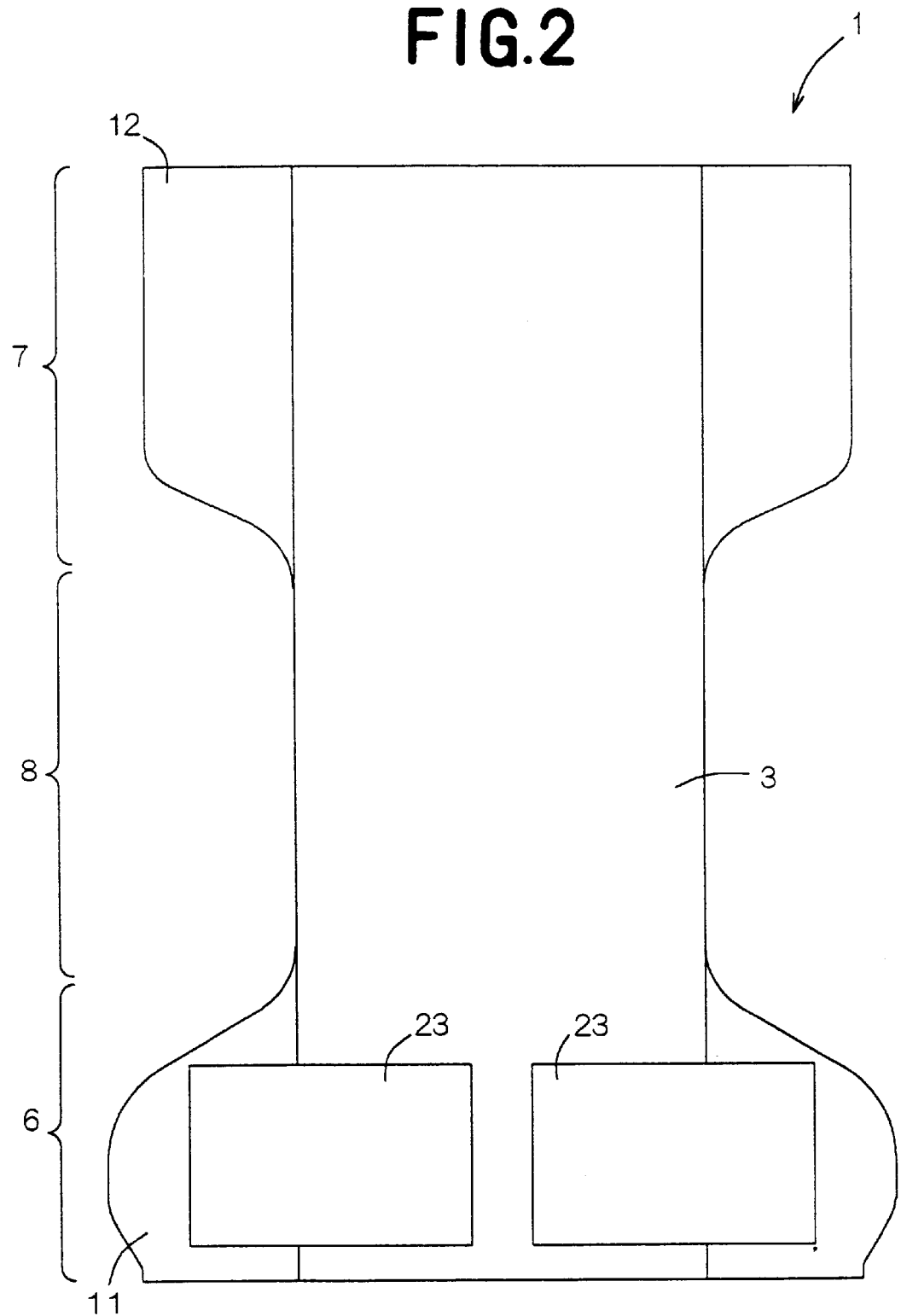
FIG. 2 is a plan view showing an outer side of the disposable diaper.

FIG. 1 is a plan view showing an inner side of a diaper 1 as partially broken away and FIG. 2 is a plan view showing the outer side of this diaper 1. The diaper 1 has a liquid-pervious topsheet 2, a liquid-impervious backsheet 3 and a liquid-absorbent core 4 disposed between these two sheets 2, 3. The diaper 1 is longitudinally (i.e., vertically as viewed in these figures) composed of a front waist region 6, a rear waist region 7 and a crotch region 8 extending between these two waist regions 6, 7. The front and rear waist regions 6, 7 are respectively formed with front wings 11 and rear wings 12 extending circumferentially outward from transversely opposite side edges thereof. Along an outer end of the rear waist region 7, a plurality of elastic members 14 extend circumferentially of the region 7 to be associated with a waist-opening. The crotch region 8 is provided along transversely opposite side edges thereof with a plurality of elastic members 16 extending longitudinally of the region 8 to be associated with respective leg-openings. These elastic members 14, 16 are disposed between the top- and backsheets 2, 3 or separately prepared sheets bonded to these top- and backsheets 2, 3, respectively, to extend and bonded under tension to one of these sheets.

A pair of ribbon-like barrier cuffs 13 longitudinally extend on the inner surface of the diaper 1 in parallel to transversely opposite side edges of the diaper 1, respectively. Each of the barrier cuffs 13 has its outer side edge portion 13b as well as its longitudinally opposite end portions fixed to the inner surface of the diaper 1 and its inner side edge portion 13a not fixed to the inner surface of the diaper 1. More specifically, the inner side edge portion 13a is folded back in envelope-like manner to wrap a longitudinally extending elastic member 17 biasing the cuff 13 to rise on the inner surface of the diaper 1 (See FIG. 5). The elastic member 17 is bonded under tension to the inner surface of the barrier cuff 13 at least at the longitudinally opposite end portions so that contraction of the elastic member 17 may cause the barrier cuff 13 to rise on the inner surface of the diaper 1 as the diaper 1 is put on a wearer's body. Thus, such barrier cuffs 13 are adapted to form a pair of pockets (not shown) opening inwardly of the diaper 1 and thereby to prevent body fluids from leaking.

The transversely opposite side edges of the rear wing 12 partially extend circumferentially outward to form respective pairs of fastener sections 21 spaced apart from each other vertically as viewed in FIGS. 1 and 2. Each of the fastener sections 21 is provided on its inner surface with a male member 22 as a component of a mechanical fastener so as to extend longitudinally thereof. FIG. 1 shows the left side fastener sections 21 as folded onto the inner surface of the rear wing 12 and the right side fastener sections 21 as extending circumferentially outward. These fastener sections 21 can be releasably anchored on the associated female members 23 at appropriate positions thereof to connect the front and rear waist regions 6, 7 to each other. These female members 23 are components of the mechanical fasteners and attached to the outer surface of the front waist region 6.

Figure 3:
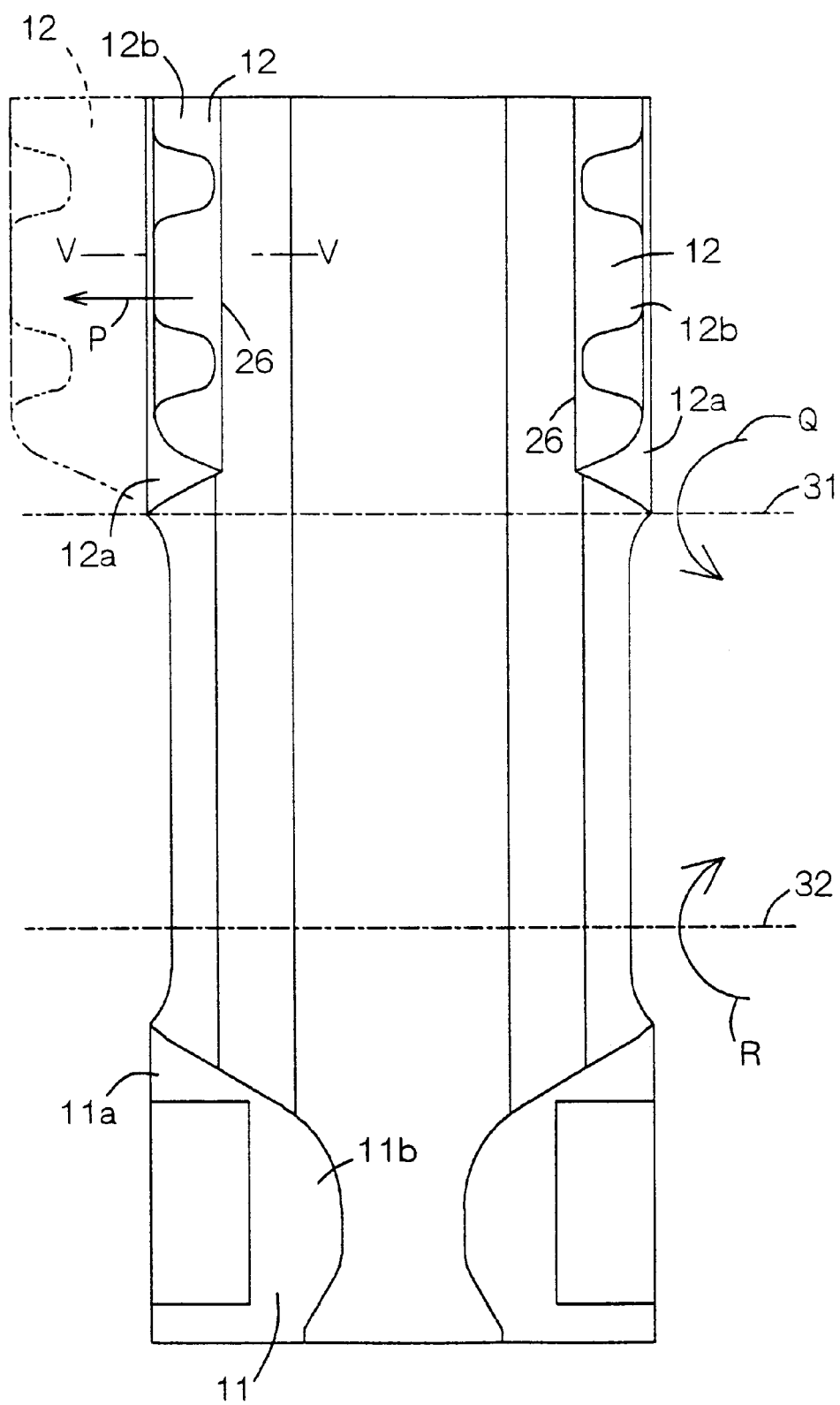
FIG. 3 is a view similar to FIG. 1 but showing the disposable diaper with its wings being folded.

FIG. 3 is a plan view showing the diaper 1 having both the front wing 11 and the rear wing 12 folded back onto the inner surface of the diaper 1 and its apparent width reduced. The front wing 11 is folded back along a proximal side edge 11a longitudinally extending in parallel to the side edge 4a (See FIG. 1) of the core. The rear wing 12 is folded back along the other side edge 4b (See FIG. 1) onto the inner surface of the diaper 1. Of the portion folded in this manner, a longitudinally extending free side edge 12b circumferentially opposed to a proximal edge 12a as well as the vicinity of the free side edge portion 12b is folded again along a fold line 26 longitudinally extending between the proximal side edge 12a and the free side edge portion 12b circumferentially outward.

Of these right and left rear wings 12 folded in this manner, one of them presents a Z-shape and the other presents an inverted Z-shape in a circumferential cross-section. The both rear wings 12 have their free side edge portions 12 extending circumferentially outward and preferably lying in the vicinity of the proximal side edges 12a. With such rear wings 12, the free side edge portions 12b may be held and pulled circumferentially outward as indicated by an arrow P to develop these rear wings 12 as indicated by chain lines.

Figure 4:
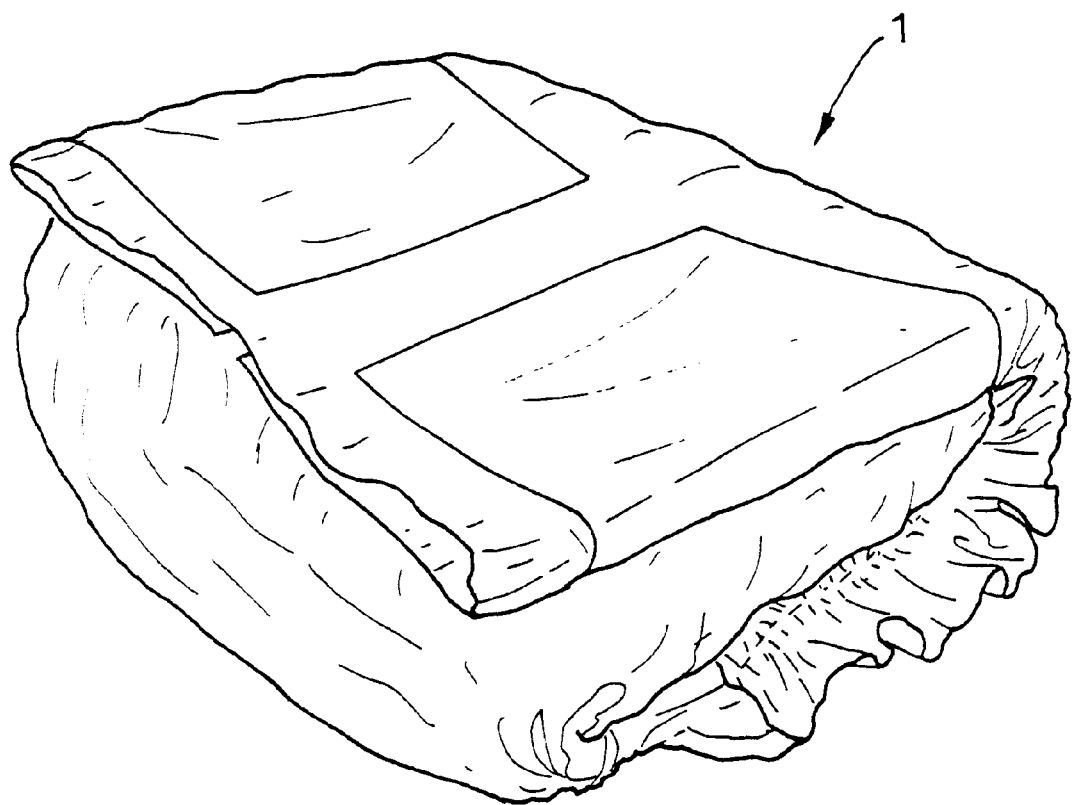
FIG. 4 is a perspective view showing the diaper in its folded state.

FIG. 4 is a perspective view showing the diaper 1 as compactly folded. Such state of the diaper 1 is achieved by folding the diaper 1 from the state of FIG. 3 along a first fold line 31 extending transversely in a direction as indicated by an arrow Q and then folding the diaper 1 along a second fold line 32 in a direction as indicated by an arrow R. In this state, the diaper 1 is packaged and supplied to the consumer.

Figure 5:
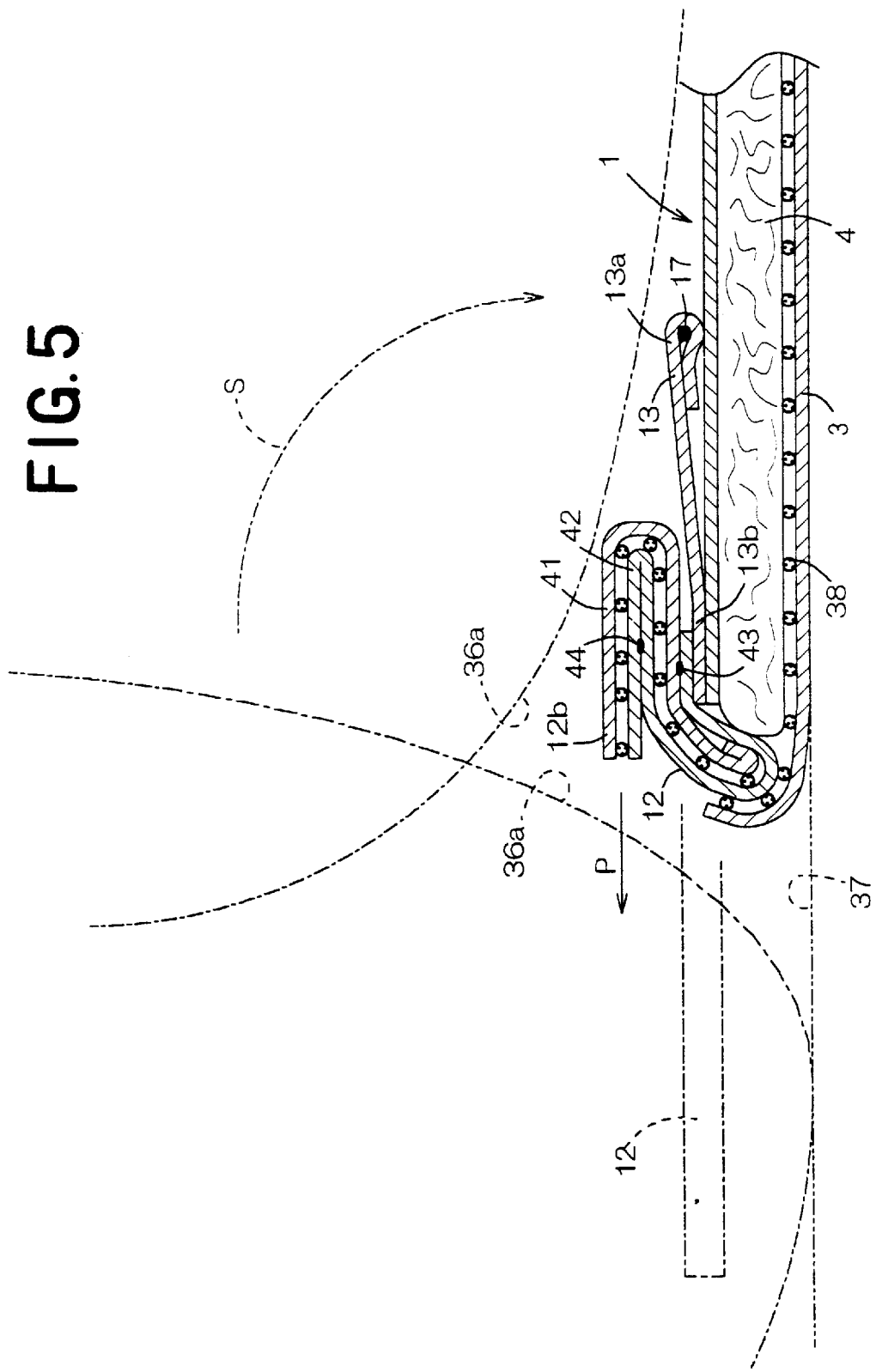
FIG. 5 is sectional view taken along a line V—V in FIG. 3.

FIG. 5 is a sectional view taken along a line V—V in FIG. 3, showing a manner in which the diaper 1 is put on the wearer's body. To wear the diaper 1 having been supplied to the consumer in the state illustrated by FIG. 4, the diaper 1 may be unfolded to the state of FIG. 3. The diaper 1 unfolded in this manner may be placed on a bed 37 so that the rear wings 12 can be sideways put against hip 36a of the wearer lying on his or her side on the bed 37. Then the wearer's body may be rolled in a direction as indicated by an arrow S until the wearer turns over on his or her back. Then, the wearer's hip 36a may be placed on the diaper 1. Thereafter, a helper may insert his or her both hands under the hip 36a and grasp the free side edge portions 12b. Thereupon, the free side edge portions 12b may pulled in opposite directions P to unfold the rear wings 12 laterally from the hip 36a. The core 4 is usually dimensioned to have substantially same width as a width of the hip 36a. This means that the wearer's body may be turned over on his or her back to position the hip 36a upon the core 4 in a substantially middle zone of the diaper 1. By following such procedure, the diaper 1 can be easily put on the wearer's body even if the wearer of the diaper 1 is an adult, particularly a bedridden adult.

Referring to FIG. 5, the core 4 and the backsheet are bonded together by means of suitable adhesive 38 such as hot melt adhesive. The wings 12 comprise inner and outer layers of nonwoven fabrics 41, 42 bonded together by means of adhesive 38. Such wings 12 are provided with the male members 22 as the components of the mechanical fasteners bonded thereto by means of adhesive or heat-sealing technique. In the wings 12 folded in Z- or inverted Z-shapes, both adhesive 43 by means of which the inner nonwoven fabric layers 41 are bonded together and adhesive 44 by means of which the outer nonwoven fabric layers 42 together are relatively weak adhesive to maintain the Z- and inverted Z-shapes. In other words, the free side edge portions 12b may be pulled in opposite directions to separate the nonwoven fabric layers 41 from each other and the nonwoven fabric layers 42 from each other without any significant resistance. If it is not required to maintain the Z- and inverted Z-shapes, this invention can be implemented without use of such adhesive 43, 44.

In view of the fact that the free side edge portions 12b of the respective rear wings 12 extend circumferentially outward, the number of times the rear wings 12 should be folded is not limited to twice and it is possible without departing from the scope of this invention to fold them twice x integer.

In the disposable diaper according to this invention, the rear wings have their free side edge portions folded on the inner surface of the diaper so as to extend circumferentially outward. This unique arrangement allows the wearer's hip to be easily placed upon the middle zone of the diaper by placing these rear wings against the hip of the diaper wearer lying on his or her side.

What is claimed is:

1. A disposable diaper comprising:

a liquid-pervious topsheet;

a liquid-impervious backsheet;

a liquid-absorbent core disposed between the liquid-pervious topsheet and the liquid-impervious backsheet;

a front waist region;

a rear waist region;

a crotch region extending between the front waist region and the rear waist region in a longitudinal direction of the diaper;

a pair of barrier cuffs extending in the longitudinal direction, each barrier cuff having a proximal edge that is fixed to an inner surface of the diaper, and a free distal edge that extends transversely inward from the proximal edge; and first wings formed on transversely opposite sides of the rear waist region and extending outward in a transversal direction intersecting said longitudinal direction, said first wings having proximal side portions extending in said longitudinal direction immediately outside transversely opposite side edges of said liquid-absorbent core and free side edge portions spaced apart from said side edges of said liquid-absorbent core which are opposed to the respective proximal side edge portions, said first wings being folded on an inner side of said diaper along fold lines extending in said longitudinal direction two or more times so that said free edge portions thereof extend outward in said transversal direction, said fold lines including fold lines located along the proximal side edge portions of the first wings, so that folded portions of the first wings extend over less that an entire width of the barrier cuffs.

2. The diaper according to claim 1, wherein said first wings are folded on the inner side of said diaper to form a Z-shape or an inverted Z-shape in a cross-section taken in said transversal direction.

3. The diaper according to claim 1, further comprising second wings formed in said front waist region and extending outward in said transversal direction, said second wings being folded onto the inner side of said diaper.

4. The diaper according to claim 1, wherein said diaper is folded back onto the inner side of said diaper after said first and second wings have been folded back onto the inner side of said diaper.

5. The diaper according to claim 1, wherein said first wings folded twice or more have their portions overlapping one another and separably bonded one to another.

6. The diaper according to claim 1, wherein the folded portions of the first wings extend over less that about one half of the entire width of the barrier cuffs.

* * * * *